United States Patent [19]

Ciganek

[11] 3,954,865
[45] May 4, 1976

[54] N-CYCLOALKYL SUBSTITUTED-10,11-DIHYDRO 5H-DIBENZO[A,D] CYCLOHEPTEN-5-IMINES

[75] Inventor: Engelbert Ciganek, Chadds Ford, Pa.

[73] Assignee: E. I. Du Pont de Nemours and Company, Wilmington, Del.

[22] Filed: Oct. 23, 1974

[21] Appl. No.: 517,224

Related U.S. Application Data

[63] Continuation-in-part of Ser. No. 248,065, April 27, 1972, abandoned, which is a continuation-in-part of Ser. No. 156,472, June 24, 1971, abandoned.

[52] U.S. Cl............................. 260/566 R; 424/325
[51] Int. Cl.²...................................... C07C 119/00
[58] Field of Search................................ 260/566 R

[56] References Cited
UNITED STATES PATENTS
3,803,234   4/1974   Dostert et al.................. 260/566 R FOREIGN PATENTS OR APPLICATIONS
2,201,089   4/1974   France........................... 260/566 R

*Primary Examiner*—Gerald A. Schwartz
*Attorney, Agent, or Firm*—A. P. Mentis

[57] ABSTRACT

5H-dibenzo[a,d]cyclohepten-5-imines having a cyclic alkyl group, such as cyclopropyl or cyclobutyl, and their 10,11-dihydro derivatives, are useful as plasticizers for polymers and also for their effect on the central nervous systems of mammals.

7 Claims, No Drawings

N-CYCLOALKYL SUBSTITUTED-10,11-DIHYDRO 5H-DIBENZO[A,D] CYCLOHEPTEN-5-IMINES

CROSS-REFERENCE TO RELATED APPLICATION

This application is a continuation-in-part of application Ser. No. 248,065 now abandoned, filed Apr. 27, 1972, which in turn is a continuation-in-part of application Ser. No. 156,472, filed June 24, 1971, now abandoned.

BACKGROUND OF THE INVENTION

Field of the Invention

This invention relates to novel cycloalkyl imines of dibenzocycloheptenes useful as plasticizers for polymers and for their effect on the central nervous system of mammals.

2. Description of Prior Art

Numerous tricyclic compounds have been made including dibenzocycloheptane derivatives. None of these have a cycloalkyl containing imino group attached to nuclear carbon of the seven membered ring. Some oximes have been reported in U.S. Pat. Nos. 3,441,608 and 3,526,631. Belgian patent No. 773,649 published Apr. 10, 1972 shows alkylamino dibenzocycloheptane imines which are different from the compounds of this invention. U.S. Pat. No. 3,780,106 issued on Dec. 18, 1973 appears to show straight chain alkyl imines of dibenzocycloheptane but does not disclose any biological or plasticizing properties.

DESCRIPTION OF THE INVENTION

The compounds of this invention have the structure

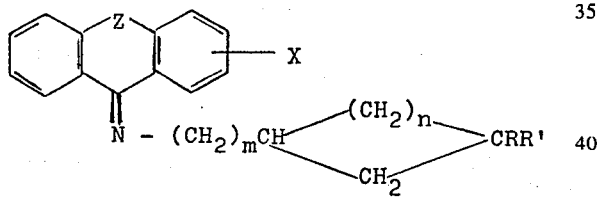

where Z is —CH$_2$CH$_2$— or —CH=CH—;

R and R' are H or alkyl having a total of no more than 4 carbons or together RR' is an alkylidene of no more than 4 carbons;

X is H or halogen; and m and n individually are 0 or 1.

The above compounds can generally exist in two isomeric forms due to the imino double bond. Both are useful for the purposes of this invention. The imino group is sufficiently basic to form acid addition salts which have increased water solubility.

The compounds of this invention include cycloheptenes of the formula

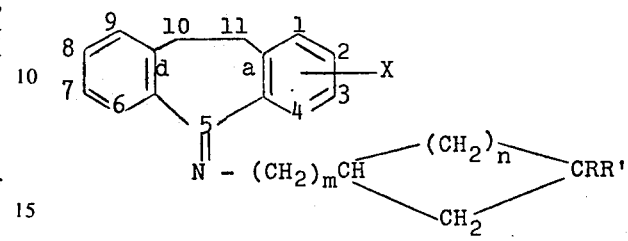

where the 10–11 positions can be a single bond or a double bond. Preferred are those which have a single bond at the 10-11 positions and in which R and R' are H and n is 0. Particularly preferred at present is the compound where Z=—CH$_2$CH$_2$-, m is 1, n is zero and X, R and R' are each H.

The imino compounds of the invention are prepared from ketones of the formula

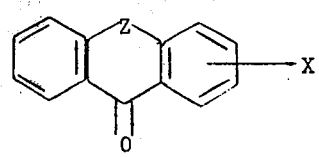

by reaction with a primary amine

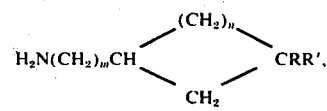

where X, Z, R, R', m and n have the values previously given, in the presence of titanium tetrachloride at a temperature of 0°–100°C., with 10°–40°C. being preferred, for times of several hours to several days. The reaction is carried out under anhydrous conditions generally with an inert diluent such as an aromatic hydrocarbon, an aliphatic ether, or hexamethylphosphoramide and is represented as follows:

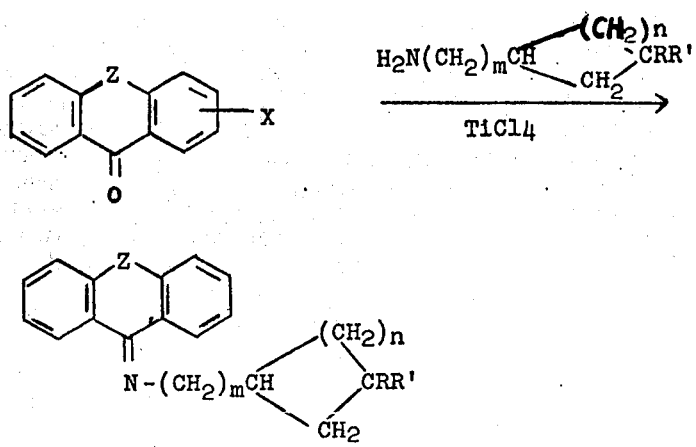

After the imine is formed, it is separated by removal of the titanium compounds by alkaline aqueous extraction and purified.

A further method reacts the aforesaid ketone compound with a lower alkyl amine such as methylamine to produce an N-methylimine. The methyl group is then replaced by a higher cyclic alkyl group, as described for instance in Example 1, whereby an acid catalyst such as a sulfonic or sulfuric acid is used at temperatures of 30°–220°C., with 100°–150° preferred, for several hours.

SPECIFIC EMBODIMENTS OF THE INVENTION

The following are illustrative examples of the invention in which all temperatures are Centigrade and all parts are by weight unless otherwise stated.

EXAMPLE 1

N-Cyclopropylmethyl-10,11-Dihydro-5H-dibenzo[a,d]cyclohepten-5-imine

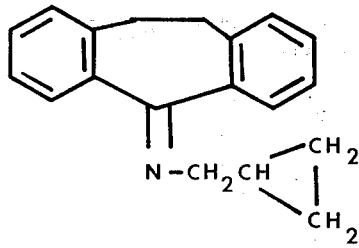

$Z = -CH_2-CH_2-$ $m = 1$ $n = 0$ $X = R = R' = H$

In a Carius tube is placed 4.52 g of N-methyl-10,11-dihydro-5H-dibenzo[a,d]cyclohepten-5-imine, 9.2 g of cyclopropylmethylamine and 0.46 g of p-toluenesulfonic acid hydrate. The tube is sealed under vacuum and heated to 120° for 60 hours. The cooled tube is opened, the excess cyclopropylmethylamine is removed under vacuum, and the resiude is dissolved in ether. The solution is washed with aqueous sodium hydroxide solution and dried. The solvent is removed, and the residue is combined with the recovered cyclopropylmethylamine and 0.43 g of p-toluenesulfonic acid hydrate. The mixture is transferred to a Carius tube which is then sealed under vacuum and heated to 120° for an additional 30 hours to complete the reaction. The mixture is worked up as described above, and the crude product is crystallized from hexane to give 3.47 g (65%) of N-cyclopropylmethyl-10,11-dihydro-5H-dibenzo[a,d]cyclohepten-5-imine, mp 98°–99°. An analytical sample (hexane) had mp 99°–100°. Nmr spectrum (in $CDCl_3$): multiplets at $\tau$ 2.1–3.0 (8H), 6.1–7.5 (6H), 8.3–9.0 (1H) and 9.1–10.0 (4H). Anal. Calcd. for $C_{19}H_{19}N$: C, 87.31; H, 7.33; N, 5.36; Found: C, 87.52; H, 7.27; N, 5.53.

The N-methyl-10,11-dihydro-5H-dibenzo[a,d]cyclohepten-5-imine was obtained as follows:

A solution of 52.5 g of titanium tetrachloride in 300 ml of anhydrous benzene is added slowly, under nitrogen, to a stirred, cooled (ice-bath) mixture of 100 g of 10,11-dihydro-5H-dibenzo[a,d]cyclohepten-5-one, 103 g of methylamine and 1200 ml of anhydrous benzene. After stirring at room temperature for 12 days the mixture is cooled, treated with concentrated aqueous sodium bicarbonate solution and filtered through Celite. The layers of the filtrate are separated, and the benzene layer is dried with magnesium sulfate. Removal of the solvent and crystallization of the residue from 200 ml of hexane gives 95.6 g (88% yield) of N-methyl-10,11-dihydro5H-dibenzo[a,d]cyclohepten-5-imine, mp 89°–90°. An analytical sample (hexane) also had mp 89°–90°. Nmr spectrum (in $CDCl_3$): multiplets at $\tau$ 2.3–3.2 (8H) and 6.8–7.2 (4H) and singlet at 6.7 (3H).

Anal. Calcd. for $C_{16}H_{15}N$: C, 86.84; H, 6.83; N, 6.33; Found: C 87.01; H, 6.63; N, 6.50.

EXAMPLE 2

N-Cyclopropyl-10,11-dihydro-5H-dibenzo[a,d]cyclohepten-5-imine

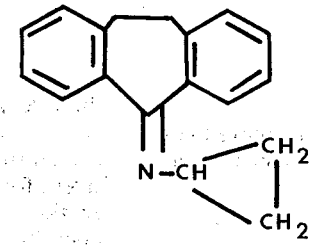

$z = -CH_2CH_2-$ $m$ and $n = 0$ $X = R = R' = H$

To a solution of 5 g of 10,11-dihydro-5H-dibenzo[a,d]cyclohepten-5-one and 20 g of cyclopropylamine in 25 ml of hexamethylphosphoramide is added, with cooling, during 30 minutes, a solution of 1.7 ml of titanium tetrachloride in 10 ml of anhydrous benzene. After stirring at room temperature for 2 weeks, benzene (50 ml) and water (50 ml) are added, with cooling. The mixture is filtered, the layers of the filtrate are separated, and the aqueous phase is extracted with 50 ml of benzene. The combined aqueous phases are washed with 5% aqueous sodium bicarbonate solution (25ml) and water (3 × 25 ml) and dried with magnesium sulfate. The solvent is removed, and the residue is shortpath distilled at a bath temperature of 145°–150° (0.3 micron) to give N-cyclopropyl-10,11-dihydro-5H-dibenzo-[a,d]cyclohepten-5-imine as a solid. Nmr spectrum (in $CDCl_3$): multiplets at $\tau$ 2.3–3.0 (8H) 6.6–7.2 (5H) and 8.2–9.4 (4H).

EXAMPLE 3

N-Cyclopropylmethyl-5H-dibenzo[a,d]cyclohepten-5-imine

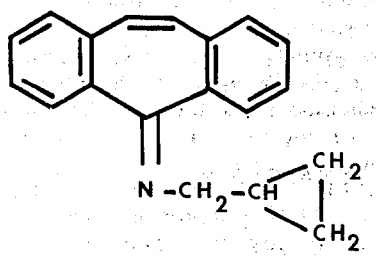

Employing the procedure of Example 1, but using N-methyl-5H-dibenzo[a,d]cyclohepten-5-imine in place of N-methyl-10,11-dihydro-5H-dibenzo[a,d]cyclohepten-5-imine gives N-cyclopropylmethyl-5H-dibenzo[a,d]cyclohepten-5-imine, containing about 10% of the starting material, and distilling at a bath temperature of 140°–150° (0.2 micron). Nmr spectrum (in CDCl$_3$): multiplet at τ 2.3–3.0 (8H); singlet at 3.2 (2H) and multiplets at 6.2–7.2 (2H) and 8.6–10.2 (5H).

N-methyl-5H-dibenzo[a,d]cyclohepten-5-imine can be obtained as follows:

Using the procedure following Example 1, a mixture of 100 g of 5H-dibenzo[a,d]-cyclohepten-5-one, 98 g of methylamine and 1000 ml of benzene is treated with 53 g of titanium tetrachloride. The mixture is worked up after stirring at room temperature for 6 days. Short-path distillation of the crude product at 120° bath temperature and 0.1 micron pressure gives 101.2 g (95% yield) of N-methyl-5H-dibenzo[a,d]cyclohepten-5-imine as a viscous oil that solidifies slowly on standing. Nmr spectrum (in CDCl$_3$): multiplet at τ 2.3–2.9 (8H) and singlets at 3.2 (2H) and 6.7 (3H).

Anal. Calcd. for C$_{16}$H$_{13}$N: C, 87.64; H, 5.98; N, 6.39; Found: C, 87.76; H, 6.05; N, 6.29.

EXAMPLE 4

3-Chloro-N-cyclopropylmethyl-10,11-dihydro-5H-dibenzocyclohepten-5-imine

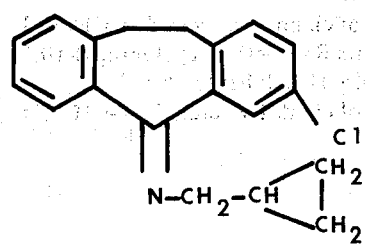

Following the procedure of Example 1, but using 3-chloro-N-methyl-10,11-dihydro-5H-dibenzo[a,d]cyclohepten-5-imine in place of N-methyl-10,11-dihydro-5H-dibenzo[a,d]cyclohepten-5-imine gives 3-chloro-N-cyclopropylmethyl-10,11-dihydro-5H-dibenzocyclohepten-5-imine (mixture of isomers), containing about 13% of unreacted starting material. It is distilled at a bath temperature of 140°–150° (0.2 micron). Nmr spectrum (in CDCl$_3$): multiplet at 2.2–3.1 (7H) and multiplets at 6.3–7.3 (6H) and 8.3–10.1 (5H).

The 3-chloro-N-methyl-10,11-dihydro-5H-dibenzo[a,d]cyclohepten-5-imine is obtained by the procedure following Example 1: A mixture of 21.89 g of 3-chloro-10,11-dihydro-5H-dibenzo[a,d]cyclohepten-5-one (S. O. Winthrop et al., J. Org. Chem., 27, 230 (1962)), 37 g of methylamine and 400 ml of benzene is treated with a solution of 8 ml of titanium tetrachloride in 50 ml of benzene. Workup after stirring at room temperature for 24 days gives 19.8 g of an oil. It is dissolved in ether and extracted with two portions of cold 5% hydrochloric acid. The acid extracts are washed with ether and carefully treated with excess aqueous sodium hydroxide. The product is extracted with methylene chloride, and the solution is washed with conc. sodium chloride solution and dried. Removal of the solvent and crystallization of the residue from hexane gives 13.3 g (58% yield) of 3-chloro-N-methyl-10,11-dihydro-5H-dibenzo[a,d]cyclohepten-5-imine, mp 84°–114°. Nmr spectrum (in CDCl$_3$): multiplets at τ 2.3–3.3 (7H) and 6.6–7.4 (4H) and singlet at 6.7 (3H). An analytical sample (hexane) had mp 84°–114°. The melting point indicates the presence of the syn and anti isomers.

Anal. Calcd. for C$_{16}$H$_{14}$ClN: C, 75.14; H, 5.52; N, 5.48; Found: C, 75.38; H, 5.56; N, 5.58.

z = -CH=CHm = 1 n = 0

X = R = R' = H z = -CH$_2$CH$_2$- m = 1 n = 0

X = Cl

R = R' = H

EXAMPLE 5

N-(3-Isopropylidenecyclobutylmethyl)-10,11-dihydro[a,d]cyclohepten-5-imine

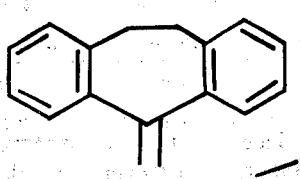

Z = -CH$_2$CH$_2$ m = 1 n = 1

RR' is =C(CH$_3$)$_2$

X = H

The general procedure of Example 1 was employed with 21.3 g of N-methyl-10,11-dihydro-5H-dibenzo[a,d]cycloheptene-5-imine, 0.34 g p-toluenesulfonic acid and 6 ml of 3-isopropylidenecyclobutylmethylamine heated under nitrogen for 60 hrs at 122°. Unreacted amine was removed by heating up to 100° at 0.1µ. The viscous oil residue was distilled (short path) at 160°–170° at 0.3µ to give 2.78 g whose nmr has multiplet at 2.2–3.2 (8H), 6.3–8.3 and singlet at 8.6.

The following 10,11-dihydro-5H-dibenzo[a,d]cyclohepten-5-ones can be employed as starting materials according to the procedures exemplified by the above examples: 1-fluoro-10,11-dihydro-5H-dibenzo[a,d]cyclohepten-5-one, and 3-bromo-10,11-dihydro-5H-dibenzo[a,d]cyclohepten-5-one.

The following amines used in the procedure of Example 1 in place of cyclopropylmethylamine: methylenecyclopropylmethylamine (obtained by reaction of methylene iodide and Zn/Cu couple with 2,3-butadienylamine), 2-n-butylcyclopropylamine, and 3,3-diethylcyclobutylamine give the following compounds respectively: N-methylenecyclopropylmethyl-10,11-dihydro-5H-dibenzo[a,d]cyclohepten-5-imine, N-(2-n-butylcyclopropyl)-10,11-dihydro-5H-dibenzo[a,d]cyclohepten-5-imine, and N-(3,3-diethylcyclobutyl)-10,11-dihydro-5H-dibenzo[a,d]cyclohepten-5-imine.

Many compounds which are active in the central nervous system of mammals appear to inhibit the uptake of catecholamines by mammalian brain tissues. Those which selectively inhibit the uptake of norepinephrine by the hypothalamus appear to be useful as antidepressants while those which selectively inhibit the uptake of dopamine by the corpus striatum appear to be useful in Parkinsons disease; Coyle et al, Science 166, 899–901 (1969). The compounds of the invention have the ability of selectively inhibiting the uptake of dopamine by the corpus striatum. This ability was measured by a test procedure following that of Coyle et al supra. Rat brain slices from the corpus striatum and hypothalamus are separately homogenized and incubated with predetermined amounts of labelled norepinephrine or dopamine and a compound of the invention. After a suitable incubation period the amount of labelled catecholamine taken up by the brain homogenate is determined. Table I below shows the molar concentration of the compounds that produced 50% inhibition of labelled catecholamine uptake ($ID_{50}$) by the brain tissues.

The compound of Example 1 is most interesting since it appears to have an almost exclusive effect inhibiting the uptake of dopamine, that is, it inhibits the uptake of dopamine without significantly inhibiting the uptake of norepinephrine. This highly selective activity enables more precise study of dopamine systems in mammals, as for example, the role of dopamine and other catecholamines in normal body functions such as sleeping and in pathological conditions such as hyperkinesia in children and Parkinsons disease, etc.

All of the new compounds of the invention are useful as plasticizers at e.g., 5–15% by weight, for polymers such as polyvinyl chloride, as illustrated by the following example.

EXAMPLE A

A sample of 0.1 g of N-cyclopropylmethyl-10,11-dihydro-5H-dibenzo[a,d]cyclohepten-5-imine is dissolved in 2 ml of a solution containing 10% by weight of polyvinyl chloride (Geon 101) in tetrahydrofuran. The film cast from this solution is plasticized and is flexible and tough. A film cast from a solution containing only polyvinyl chloride and tetrahydrofuran is stiff and brittle.

The embodiments of the invention in which an exclusive property or privilege is claimed are defined as follows:

1. A compound of the structure

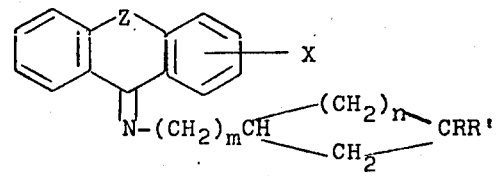

wherein Z is $-CH_2CH_2-$ or $-CH=CH-$;
R and R' are H;
X is hydrogen or halogen and
m and n individually are 0 or 1.

2. A compound according to claim 1 wherein Z is $-CH_2-CH_2-$.

3. A compound according to claim 1 wherein Z is $-CH=CH-$.

4. A compound according to claim 2 wherein X is H.

5. The compound of claim 1 wherein X is H, Z = $-CH_2-CH_2-$, m=1, n=0, and R and R' are H; N-cyclopropylmethyl-10,11-dihydro-5H-dibenzo[a,d]cyclohepten-5-imine.

6. The compound of claim 1 wherein Z = $-CH_2-CH_2-$, X is H, m and n=0 and R=R'=H; N-cyclopropyl-10,11-dihydro-5H-dibenzo[a,d]cyclohepten-5-imine.

7. The compound of claim 1 wherein Z = $-CH_2-CH_2-$, m=1, n=0, X=Cl and R=R'=H; 3-chloro-N-cyclopropylmethyl-10,11-dihydro-5H-dibenzo[a,d]cyclohepten-5-imine.

TABLE I

| Compound of Example | Group on Imino N | Z | X | $ID_{50}$ Striatum | $ID_{50}$ Hypothalmus | Ratio Hypothalmus/Striatum |
|---|---|---|---|---|---|---|
| 1 | Cyclopropyl-methyl | $CH_2-CH_2$ | H | $5 \times 10^{-7}$M | $1 \times 10^{-5}$M | 20 |
| 2 | Cyclopropyl | $CH_2-CH_2$ | H | $1.7 \times 10^{-5}$M | $>1 \times 10^{-4}$M | >6 |
| 3 | Cyclopropyl-methyl | $CH=CH$ | H | $1 \times 10^{-5}$M | $3.8 \times 10^{-6}$M | .38 |
| 4 | Cyclopropyl-methyl | $CH_2-CH_2$ | Cl | $1 \times 10^{-6}$M | $2 \times 10^{-6}$M | 2 |
| 5 | Isopropylidene-cyclobutylmethyl | $CH_2-CH_2$ | H | $8 \times 10^{-6}$M | $1 \times 10^{-5}$M | 1.25 |
| — | Isopropyl[1] | $CH_2-CH_2$ | H | $8 \times 10^{-6}$M | $2 \times 10^{-6}$M | 0.25 |

[1] Prior art compound of U.S. patent 3,780,106